(12) United States Patent
Poduslo et al.

(10) Patent No.: US 7,988,969 B2
(45) Date of Patent: Aug. 2, 2011

(54) TREATMENT FOR CENTRAL NERVOUS SYSTEM DISORDERS

(75) Inventors: Joseph F. Poduslo, Rochester, MN (US); Geoffry L. Curran, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/550,944

(22) Filed: Aug. 31, 2009

(65) Prior Publication Data
US 2009/0324492 A1    Dec. 31, 2009

Related U.S. Application Data

(63) Continuation of application No. 10/796,522, filed on Mar. 9, 2004, now abandoned, which is a continuation of application No. 09/942,253, filed on Aug. 29, 2001, now abandoned.

(51) Int. Cl.
*A61K 39/395* (2006.01)
*A61K 39/00* (2006.01)
*A61K 39/385* (2006.01)

(52) U.S. Cl. ............... 424/145.1; 424/130.1; 424/192.1; 424/193.1; 424/194.1; 514/1.1; 514/21.2; 514/17.8

(58) Field of Classification Search ......................... None
See application file for complete search history.

(56) References Cited

U.S. PATENT DOCUMENTS

| | | | |
|---|---|---|---|
| 4,946,778 A | 8/1990 | Ladner et al. |
| 5,231,000 A | 7/1993 | Majocha et al. |
| 5,260,308 A | 11/1993 | Poduslo et al. |
| 5,262,332 A | 11/1993 | Selkoe |
| 5,604,198 A | 2/1997 | Poduslo et al. |
| 5,670,477 A | 9/1997 | Poduslo et al. |
| 5,854,204 A | 12/1998 | Findeis et al. |
| 2003/0082191 A1 | 5/2003 | Podulso |
| 2004/0022736 A1 | 2/2004 | Poduslo et al. |
| 2004/0142872 A1 | 7/2004 | Poduslo |

FOREIGN PATENT DOCUMENTS

| | | |
|---|---|---|
| WO | WO 95/11311 | 4/1995 |
| WO | WO-96/40248 | 12/1996 |
| WO | WO 99/27944 | 6/1999 |
| WO | WO 01/74374 | 10/2001 |
| WO | WO-02/42462 | 5/2002 |
| WO | WO 02/42462 | 5/2002 |

OTHER PUBLICATIONS

Huse, WD et al., "Generation of a large combinatorial library of the immunoglobulin repertoire in phage lambda," Science, Dec. 8, 1989, 246: 1275-1281.

Vallette, F et al., "Construction of mutant and chimeric genes using the polymerase chain reaction," Nucl. Acids Res., 1989, 17: 723-733.
de St Groth SF and Scheidegger D, "Production of monoclonal antibodies: strategy and tactics," J Immunol. Methods, 1980, 35(1-2):1-21.
European Search Report (Supplementary), EP 02761522, European Patent Office, Nov. 14, 2007.
Bickel et al., Development and in vitro characterization of a cationized monoclonal antibody against beta A4 protein: a potential probe for Alzheimer's disease, Bioconj. Chem., 5:119-125, 1994.
European Search Report (Supplementary, Partial), EP 02761522.8, European Patent Office, Jun. 29, 2007.
Poduslo et al., Amyloid beta peptide as a vaccine for Alzheimer's disease involves receptor-mediated transport at the blood-brain barrier, Neuroreport, 12(15):3197-3200, 2001.
Wu et al., Drug targeting of a peptide radiopharmaceutical through the primate blood-brain barrier in vivo with a monoclonal antibody to human insulin receptor, J. Clin. Invest., 100(7):1804-1812, 1997.
Zlokovic et al., Glycoprotein 330-megalin: probable role in receptor-mediated transport of apolipoprotein J alone and in a complex with Alzheimer disease amyloid beta at the blood-cerebrospinal fluid barriers, Proceedings of the National Academy of Sciences of USA, 93(9):4229-4234, 1996.
Caravan et al., "Gadolinium (III) Chelates as MRI Contrast Agents: Structure, Dynamics, and Applications," Chem. Rev., 1999, 99:2293-2352.
Chen et al., "A learning deficit related to age and β-amyloid plaques in a mouse model of Alzheimer's disease," Nature, 2000, 408:975-979.
Curtet et al., "Polylysine-Gd-DTPA, and Polylysine-Gd-DOTA,, Coupled to Anti-CEA F(ab')$_2$ Fragments as Potential Immunocontrast Agents," Invest. Radiol., 1998, 33(10):752-761.
De St. Groth and Scheidegger, "Production of Monoclonal Antibodies: Strategies and Tactics," J. Immunol. Methods, 1980, 35:1-21.
DeMattos et al., "Peripheral anti-Aβ antibody alters CNS and plasma Aβ clearance and decreases brain Aβ burden in a mouse model of Alzheimer's disease," Proc. Natl. Acad. Sci. USA, 2001, 98(15):8850-8855.
Fraser et al., "Fibril Formation by Primate, Rodent, and Dutch-Hemorrhagic Analogues of Alzheimer Amyloid β-Protein," Biochemistry, 1992, 31:10716-10723.
Hilbich et al., "Human and rodent sequence analogs of Alzheimer's amyloid βA4 share similar properties and can be solubilized in buffers of pH 7.4," Eur. J. Biochem., 1991, 201:61-69.
Janus et al., "Aβ peptide immunization reduces behavioural impairment and plaques in a model of Alzheimer's disease," Nature, 2000, 408:979-982.
Kalra, "Circumventing leptin resistance for weight control," Proc. Natl. Acad. Sci. USA, 2001, 98(8):4279-4281.
Lauffer et al., "Preparation and Water Relaxation Properties of Proteins Labeled with Paramagnetic Metal Chelates," Magn. Reson. Imaging, 1985, 3:11-16.
Le et al., "Amyloid β$_{42}$ Activates a G-Protein-Coupled Chemoattractant Receptor, FPR-Like-1," J. Neuroscience, 2001, 21:1-5.
Morgan et al., "Aβ peptide vaccination prevents memory loss in an animal model of Alzheimer's disease," Nature, 2000, 408:982-985.
Müller-Gartner, "Imaging techniques in the analysis of brain function and behaviour," TIB Tech., 1998, 16:122-130.

(Continued)

Primary Examiner — Olga N Chernyshev
(74) Attorney, Agent, or Firm — Quarles & Brady, LLP

(57) ABSTRACT

Compositions that include an Aβ polypeptide linked to a non-Aβ polypeptide are described, as well as methods of using such compositions.

9 Claims, No Drawings

OTHER PUBLICATIONS

Poduslo and Curran, "Increased permeability across the blood-nerve barrier of albumin glycated in vitro and in vivo from patients with diabetic polyneuropathy," *Proc. Natl. Acad. Sci. USA*, 1992, 89:2218-2222.

Poduslo et al., "Macromolecular permeability across the blood-nerve and blood-brain barriers," *Proc. Natl. Acad. Sci. USA*, 1994, 91:5705-5709.

Poduslo and Curran, "Polyamine Modification Increases the Permeability of Proteins at the Blood-Nerve and Blood-Brain Barriers," *J. Neurochemistry*, 1996, 66:1599-1609.

Poduslo et al., "Permeability of Proteins at the Blood-Brain Barrier in the Normal Adult Mouse and Double Transgenic Mouse Model of Alzheimer's Disease," *Neurobiol. Disease*, 2001, 8:555-567.

Saito et al., "Vector-mediated delivery of $^{125}$I-Labeled β-amyloid peptide AB$^{1-40}$ through the blood-brain barrier and binding to Alzheimer disease amyloid of the Aβ$^{1-40}$/vector complex," *Proc. Natl. Acad. Sci. USA*, 1995, 92:10227-10231.

Saji, "Targeted Delivery of Radiolabeled Imaging and Therapeutic Agents: Bifunctional Radiopharmaceuticals," *Crit. Rev. Ther. Drug Carrier Syst.*, 1999, 16(2):209-244.

Sipkins et al., "Detection of tumor angiogenesis in vivo by $\alpha_v\beta_3$-targeted magnetic resonance imaging," *Nature Med.*, 1998, 4(5):623-626.

Wang et al., "Comparing the hypothalamic and extrahypothalamic actions of endogenous hyperleptinemia," *Proc. Natl. Acad. Sci. USA*, 1999, 96:10373-10378.

Zanusso et al., "Prion protein expression in different species: Analysis with a panel of new mAbs," *Proc. Natl. Acad. Sci. USA*, 1998, 95:8812-8816.

Foldi et al., "The Test for Severe Impairment: Validity with the Dementia Rating Scale and Utility as a Longitudinal Measure", The Clinical Neuropsychologist, 1999, 13(1):22-29.

McKhann et al., "Clinical diagnosis of Alzheimer's disease: Report of the NINCDS-ADRDA Work Group* under the auspices of Department of Health and Human Services Task Force on Alzheimer's Disease", Neurology, 1984, 34 (7):939-944.

Folstein et al., ""Mini-mental state". A practical method for grading the cognitive state of patients for the clinician", J Psychiatr Res., 1975, 12(3):189-198.

Wilkison et al., "Psychogeriatric Dependency Rating Scales (PGDRS), A Method of Assessment for Use by Nurses", Brit. J. Psychiat. ( 1980), 137:558-565.

Juva et al., "Staging the severity of dementia: comparison of clinical (CDR, DSM-III-R), functional (ADL, IADL) and cognitive (MMSE) scales", Acta Neurol. Acand., 1994, 90:293-298.

SEQUENCE LISTING

```
<160> NUMBER OF SEQ ID NOS: 1

<210> SEQ ID NO 1
<211> LENGTH: 43
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```

TREATMENT FOR CENTRAL NERVOUS SYSTEM DISORDERS

CROSS-REFERENCE TO RELATED APPLICATIONS

This application is a continuation of U.S. application Ser. No. 10/796,522 filed Mar. 9, 2004, which is a continuation of U.S. application Ser. No. 09/942,253 filed Aug. 29, 2001. All applications are incorporated by reference herein.

TECHNICAL FIELD

This invention relates to compositions for treating central nervous system (CNS) disorders such as Alzheimer's disease (AD), and more particularly, to compositions that contain a β amyloid (Aβ) polypeptide linked to a non-Aβ polypeptide.

STATEMENT REGARDING FEDERALLY SPONSORED RESEARCH OR DEVELOPMENT

Not applicable.

BACKGROUND

Both active and passive immunization involving Aβ peptides or specific monoclonal antibodies against these peptides have been assessed for the treatment and prevention of AD. Reducing Aβ accumulation by active immunization improves cognitive performance in mice. See, for example, Chen et al., *Nature*, 408:975-979 (2000); Janus et al. *Nature*, 408:979-982 (2000). The mechanism by which host-generated antibodies against Aβ clear brain senile plaques is far from being understood. Active immunization experiments use complete Freund's adjuvant, which, by itself, induces leakage of serum proteins, including IgG, through the blood-brain barrier (BBB) 2-3 weeks after injection and cannot be used as an adjuvant in humans. Passive immunization studies are confounded by the integrity of the BBB, which restricts passage of immunoglobulins. The permeability coefficient×surface area (PS) product of IgG has been quantified in rats and found to be very low ($0.03$-$0.1 \times 10^{-6}$ mg/sec) and is consistent with a transport mechanism of passive diffusion of fluid-phase endocytosis.

SUMMARY

The invention is based on the discovery that Aβ-immune complexes are transported across the BBB via a receptor-mediated process at a rate greater than that of antibody alone. Thus, transport of antibodies having specific binding affinity for Aβ across the BBB, or other polypeptides that have low permeability at the BBB, can be enhanced when linked to an Aβ polypeptide. As a result, the success of passive immunization and therapy for AD as well as other CNS disorders is enhanced. Polyamine modified antibodies having specific binding affinity for Aβ also have increased permeability at the BBB and can be used for passive immunization and treatment of AD.

In one aspect, the invention features a composition that includes an Aβ polypeptide and a non-Aβ polypeptide, wherein the Aβ polypeptide and the non-Aβ polypeptide are linked (e.g. covalently). The composition further can include a pharmaceutically acceptable carrier or excipient. The non-Aβ polypeptide can be an antibody or a fragment thereof (e.g. a Fab fragment, a single chain Fv antibody fragment, or a F(ab)$_2$ fragment). The antibody can be labeled with a radioisotope or a contrast agent. The antibody can have specific binding affinity for amyloid. The non-Aβ polypeptide also can be enzyme such as an antioxidant enzyme (e.g. catalase or superoxide dismutase), a cytokine such as an interferon, an interleukin, or a neurotrophic factor, or leptin. The Aβ polypeptide can include residues 1-40, 1-42, or 1-43 of SEQ ID NO:1.

The invention also features a method of treating a patient diagnosed with AD. The method includes administering to the patient an amount of a composition effective to treat AD, wherein the composition includes an Aβ polypeptide and antibody having specific binding affinity for the Aβ polypeptide. The antibody can be Fab fragment, a single chain Fv antibody fragment, or a F(ab)$_2$ fragment.

In another aspect, the invention features a method of treating a patient diagnosed with AD. The method includes administering to the patient an amount of an antibody effective to treat AD, wherein the antibody is polyamine modified and has specific binding affinity for an AD polypeptide.

In yet another aspect, the invention features a method of diagnosing AD in a patient. The method includes administering a composition to the patient, wherein the composition includes an Aβ polypeptide and antibody having specific binding affinity for amyloid, wherein the antibody is labeled, and detecting the presence or absence of the antibody bound to the amyloid in the brain of the patient, wherein the patient is diagnosed with AD based on the presence of labeled amyloid, (e.g., labeled amyloid deposits such as β-amyloid plaques). The detecting step can include diagnostic imaging (e.g., positron emission tomography, gamma-scintigraphy, single photon emission computerized tomography, magnetic resonance imaging, functional magnetic resonance imaging, or magnetoencephalography). Magnetic resonance imaging is particularly useful. The antibody can be labeled with a contrast agent (e.g., gadolinium, dysprosium, or iron). Gadolinium is a particularly useful contrast agent.

Unless otherwise defined, all technical and scientific terms used herein have the same meaning as commonly understood by on of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features compositions containing Aβ polypeptides that can be used to enhance transport of non-Aβ polypeptides across the BBB. As described herein, BBB permeability of a composition containing Aβ bound to a monoclonal antibody was significantly greater than that of the monoclonal antibody alone. Without being bound by a particular mechanism, Aβ itself may be responsible for transporting the antibody across the BBB. Thus, Aβ can be used to enhance the permeability of other polypeptides a the BBB, and as a result, compositions of the invention can be used in the diagnosis, treatment, and/or prevention of neurodegenerative disorders as AD, Parkinson's disease, frontotemporal dementias (e.g., Pick's disease), and amyloidotic polyneuropathies, transmissible spongiform encephalopathies (i.e., prion diseases) such as Creutzfeldt-Jakob disease (CJD), Gerstmann-Straiussler-Scheinker syndrome, and fatal familial insomnia, demyelinating diseases such as multiple sclerosis, and amyotropic lateral sclerosis.

Aβ Compositions

Compositions of the invention include a purified Aβ polypeptide linked a purified non-Aβ polypeptide. As used herein, the term "purified" refers to a polypeptide that is separated from cellular components (e.g., other polypeptides, lipids, carbohydrates, and nucleic acids) that are naturally associated with the polypeptide. Thus, a purified polypeptide is any polypeptide that is removed from its natural environment and is at least 75% pure (e.g., at least about 80, 85, 90, 95 or 99% pure). Typically, a purified polypeptide will yield a single major band on a non-reducing polyacrylamide gel.

As used herein, "Aβ polypeptide" refers to 1) the naturally occurring human Aβ polypeptide (DAE-FRHDSGY EVH-HQKLVFF AEDVGSNKGA IIGLMVGGVV IAT, SEQ ID NO:1) 2) polypeptides having one or more substitutions or insertions in the amino acid sequence of the naturally occurring human Aβ polypeptide that retain the ability to cross the BBB, and 3) fragments of 1) and 2) that retain the ability to cross the BBB. Permeability of an Aβ polypeptide at the BBB can be assessed according to the methods of Example 1. See also Poduslo et al., *Proc. Natl. Acad. Sci USA*, 89:2218-2222 (1992) and Poduslo et al., *Neurobiol. Disease* 8:555-567 (2001). The naturally-occurring human Aβ polypeptide ranges in length from 39 to 43 amino acids (residues 1 to 39, 1 to 40, 1 to 41, 1 to 42, or 1 to 43 of SEQ ID NO:1) and is a proteolytic cleavage product of amyloid precursor protein (APP). Non-limiting examples of amino acid substitutions that can be introduced into human Aβ polypeptide at amino acid residues 5, 10, 13, 19 and 20 of SEQ ID NO:1, or combinations thereof. In particular, a glycine can be substituted for the arginine at residue 5, a phenylalanine can be substituted for the tyrosine at residue 10, or an arginine can be substituted for the histidine at residue 13. Such substitutions do not alter the properties of human Aβ polypeptide. See Fraser et al., *Biochemistry*, 31:10716-10723 (1992); and Hilbich et al., *Eur. J. Biochem.* 201:61-69 (1992). An isoleucine, leucine, threonine, serine, alanine, valine, or glycine can be substituted for the phenylalanine residues at positions 19 and 20.

Suitable fragments of Aβ polypeptides are about 6 to 38 amino acid residues in length (e.g., 10 to 36, 10 to 34, 10 to 30, 12 to 28, 14 to 26, 16 to 24, or 18 to 22 amino acid residues in length) and retain the ability to cross the BBB. For example, an Aβ polypeptide may contain residues 1 to 10, 1 to 15, 1 to 20, 5 to 15, 5 to 20, 5 to 25, 10 to 20, 10 to 25, 10 to 30, or 15 to 35 of SEQ ID NO:1. Alternatively, an Aβ polypeptide may include residues 20 to 30, 20 to 35, 20 to 40, 25 to 35, 25 to 40, 30 to 40, 25 to 42, or 30 to 42 of SEQ ID NO:1.

Aβ polypeptide can be linked to non-Aβ polypeptide via covalent links. Covalent cross-linking techniques are known in the art. See, for example, "Chemistry of Protein Conjugation and Cross-linking", Shan S. Wong, CRC Press, Ann Arbor, 1991. Suitable cross-linking reagents do not interfere with the binding of the Aβ polypeptide to its cognate receptor and are chosen for appropriate reactivity, specificity, spacer arm length, membrane permeability, cleavability, and solubility characteristics. Similarly, suitable cross-linking reagents do not interfere with binding of a non-Aβ polypeptide to its binding partner (e.g., cognate receptor or epitope on a macromolecule). Cross-linking reagents are available commercially from many sources including Pierce Chimcal Co., Rockford, Ill.

An Aβ polypeptide and a non-Aβ polypeptide can be covalently cross-linked using, for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

Alternatively, an Aβ polypeptide can be linked to a non-Aβ polypeptide such as an antibody via the specific binding affinity of the antibody for the Aβ polypeptide. Purified Aβ polypeptide and antibody can be incubated together at 37° C. in an appropriate buffer (e.g., phosphate buffered saline) to form an immune complex. Such an immune complex constitutes a composition of the invention.

Aβ polypeptides can be linked to any non-Aβ polypeptide, and in particular, to any polypeptide that is useful for diagnosing or treating a disorder of the CNS. Non-Aβ polypeptides are at least six amino acid residues in length. For example, an Aβ polypeptides can be linked to an enzyme such as an antioxidant enzyme, which can protect cells against reactive oxygen species. Non-limiting examples of antioxidant enzyme includes catalase (E.C. 1.11.1.6), superoxide dismutase (E.C. 1.15.1.1), glutathione peroxidase (E.C. 1.6.4.2) and glutathione (E.C. 1.11.1.9).

Aβ polypeptides can also be linked to cytokines, such as an interferon (e.g., interferon α, β or γ), interleukin (IL) (e.g., IL-1a or b, IL-2, IL-3, IL-4, IL-5, IL-6, IL-7, IL-8, IL-9, IL-10, IL-11 or IL-12), neurotrophic factors such as neurotrophins (e.g., nerve growth factor or brain-derived neurotrophic factor), neuropoietic factors such as cholinergic differentiation factor, ciliary neurotrophic factor, oncostatin M, growth-promoting factor, and sweat gland factor, and growth factor peptides such as glial-cell line-derived neurotrophic factor, or a hormone such as leptin.

In addition, Aβ polypeptides can be linked to an antibody. For example, an Aβ polypeptide can be linked to an antibody having specific binding affinity for amyloid deposits of Aβ or of a prion protein (PrP). See U.S. Pat. No. 5,231,000 and U.S. Pat. No. 5,262,332 for examples of antibodies having specific binding affinity for Aβ. See Zanusso et al., *Proc. Natl. Acad. Sci USA* 95:8812-8816 (1998) for examples of antibodies having specific binding affinity for the protease resistant form of PrP. As used herein, the term "antibodies" includes polyclonal or monoclonal antibodies, humanized or chimeric antibodies, and antibody fragments such as single chain Fv antibody fragments, Fab fragments and F(ab)$_2$ fragments. Monoclonal antibodies are particularly useful. A chimeric antibody is a molecule in which different portions are derived from different animal species, such as those having a variable region derived from a murine monoclonal antibody and a human immunoglobulin constant region. Chimeric antibodies can be produced through standard techniques.

Antibody fragments can be generated by known techniques. For example, F(ab')$_2$ fragments can be produced by pepsin digestion of the antibody molecule, and Fab fragments can be generated by reducing the disulfide bridges of F(ab')$_2$ fragments. Alternatively, Fab expression libraries can be constructed. See, for example, Huse et al., *Science*, 246:1275 (1989). Single chain Fv antibody fragments are formed by linking the heavy and light chain fragments of the Fv region via an amino acid bridge (e.g., 15 to 18 amino acids), resulting in a single chain polypeptide. See, for example, U.S. Pat. No. 4,946,778.

In some embodiments, the Aβ polypeptide and/or the non-Aβ polypeptide are labeled to facilitate diagnosis of a CNS disorder. Typical labels that are useful include radioisotopes and contrast agent used for imaging procedures in humans. Non-limiting examples of labels include radioisotope such as $^{123}$I (iodine), $^{18}$F (fluorine), $^{99m}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. Polypeptides can be labeled through standard techniques. For example, polypeptides can be iodinated using chloramine T or 1,3,4,6-tetrachloro-3α, 6α-dephenylglycouril. For fluorination, polypeptides are synthesized and fluorine is added during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes.

Polypeptides can also be labeled with a contrast agent through standard techniques. For example, polypeptides can be labeled with Gd by conjugating low molecular Gd chelates such as Gd diethylene triamine pentaacetic acid (GdDTPA) or Gd tetraazacyclododecanetetraacetic (GdDOTA) to the polypeptides. See, Caravan et al., Chem. Rev. 99:2293-2352 (1999) and Lauffer et al., J. Magn. Reson. Imaging, 3:11-16 (1985). Antibodies can be labeled with Gd by, for example, conjugating polylysine-Gd chelates to the antibody. See, for example, Curtet et al., Invest. Radiol., 33(10):752-761 (1998). Alternatively, antibodies can be labeled with Gd by incubating paramagnetic polymerized liposomes that include Gd chelator lipid with avidin and biotinylated antibody. See, for example, Sipkins et al., Nature Med., 4:623-626 (1998).

Nucleic Acids Encoding Aβ and Non-Aβ Polypeptides

Isolated nucleic acid molecules encoding Aβ and non-Aβ polypeptides of the invention can be produced by sequence corresponding to part or all of a gene encoding an Aβ and Non-Aβ polypeptide, but free of sequences that normally flank one or both sides of the wild-type gene in a mammalian genome. An isolated nucleic acid can be, for example, a recombinant DNA molecule, provided one or both of the nucleic acid sequences normally found immediately flanking that DNA molecule in a naturally-occurring genome is removed or absent. Thus, isolated nucleic acids include, without limitation, a DNA that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid. A nucleic acid existing among hundreds to millions of other nucleic acids within, for example, cDNA or genomic libraries, or gel slices containing a genomic DNA restriction digest, is not to be considered an isolated nucleic acid.

Isolated nucleic acid molecules are at least about 18 nucleotides in length. For example, the nucleic acid molecule can be about 18 to 20, 20-50, 50-100, or greater than 150 nucleotides in length. Nucleic acid molecules can be DNA or RNA, linear or circular, and in sense or antisense orientation.

Specific point changes can be introduced into the nucleic acid sequence encoding the naturally-occurring human Aβ polypeptide by, for example, oligonucleotide-directed mutagenesis. In this method, a desired change is incorporated into an oligonucleotide, which then is hybridized to the wild-type nucleic acid. The oligonucleotide is extended with a DNA polymerase, creating a heteroduplex that contains a mismatch at the introduced point change, and a single-stranded nick at the 5' end, which is sealed by a DNA ligase. The mismatch is repaired upon transformation of E. coli or other appropriate organism, and the gene encoding the modified vitamin K-dependent polypeptide can be re-isolated from E. Coli or other appropriate organism. Kits for introducing site-directed mutations can be purchased commercially. For example, Muta-Gene® in-vitro mutagenesis kits can be purchased from Bio-Rad Laboratories, Inc. (Hercules, Calif.).

Polymerase chain reaction (PCR) techniques also can be used to introduce mutations. See, for example, Vallette et al., Nucleic Acids Res., 17(2):723-733 (1989). RCR refers to a procedure or technique in which target nucleic acids are amplified. Sequence information from the ends of the region of interest or beyond typically is employed to design oligonucleotide primers that are identical in sequence t opposite strands of the template to be amplified, whereas for introduction of mutations, oligonucleotides that incorporate the desired change are used to amplify the nucleic acid sequence of interest. PCR can be used to amplify specific sequences from DNA as well as RNA, including sequences from total genomic DNA or total cellular RNA. Primers are typically 14 to 40 nucleotides in length, but an range from 10 nucleotides to hundreds of nucleotides in length. General PCR techniques are described, for example, in PCR Primer: A Laboratory Manual, Ed. By Dieffenbach, C. and Dveksler, G., Cold Spring Harbor Laboratory Press, 1995.

Nucleic acids encoding Aβ and non-Aβ polypeptides also can be produced by chemical synthesis, either as a single nucleic acid molecule or as a series of oligonucleotides. For example, one or more pairs of long oligonucleotides (e,g, >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

Producing Purified Polypeptides

Purified Aβ and non-Aβ polypeptides of the invention can be obtained from commercial sources, or alternatively, can be obtained by extraction from a natural source (e.g., liver tissue), chemical synthesis, or by recombinant production in a host cell. In general, recombinant polypeptides are produced by introducing an expression vector that contains a nucleic acid encoding the polypeptide of interest operably linked to regulatory elements necessary for expression of the polypeptide into a bacterial or eukaryotic host cell (e.g., insect, yeast, or mammalian cells). Regulatory elements do not typically encode a gene product, but instead affect the expression of the nucleic acid sequence. In bacterial systems, a strain of Escherichia coli such as BL-21 can be used. Suitable E. coli vectors include the PGEX series of vectors that produce fusion proteins with glutathione S-transferase (GST). Transformed E. coli are typically grown exponentially then stimulated with isopropylthiogalactopyranoside (IPTG) prior to harvesting. Such fusion proteins typically are soluble and can be purified easily from lysed cells by adsorption to glutathione-agarose beads followed by elution in the presence of free glutathione. The PGEX vectors are designed to include thrombin or factor Xa protease cleavage sites so that the cloned target gene product can be release from the GST moiety.

In eukaryotic host cells, a number of viral-based expression systems can be utilized to produce the polypeptides of interest. A nucleic acid encoding a polypeptide of the invention can be cloned into, for example, a baculoviral vector such as pBlueBac (Invitrogen, San Diego, Calif.) and then used to co-transfect insect cells such as Spodoptera fugiperda (Sf9) cells with wild-type DNA from Autographa california multinuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based vector that contains a selectable marker and standard techniques. For example, the eukaryotic expression vector pCR3.1 (Invitrogen, San Diego, Calif.) can be used to express polypeptides of interest in, for example, Chinese hamster ovary (CHO) cells, COS-1 cells, human embryonic kidney 293 cells, NIH3T3 cells, BHK21 cells, MDCK cells, and human vascular endothelial cells (HU-VEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, A nucleic acid encoding a polypeptide of interest can be ligated into mammalian expression vector such as pcDNA3 (Invitrogen, San Diego, Calif.) then transcribed and translated in vitro using wheat germ extract or rabbit reticulocyte lysate.

Polypeptides of interest can be purified by known chromatographic methods including DEAE ion exchange, gel filtration, and hydroxylapatite chromatography. Polypeptides can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase. Immunoaffinity chromatography also can be used to purify polypeptide of interest.

Polyamine Modified Antibodies

As described herein, polyamine modification of an antibody having specific binding affinity for Aβ enhances permeability of the modified antibody at the BBB. In particular, polyamine-modified monoclonal antibody against Aβ has a PS product that is 36 fold higher in the cortex compared to unmodified antibody and may provide a better approach to passive immunization for AD. Antibodies having specific binding affinity for Aβ can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_XH_YN_Z$, can be cyclic or acyclic, branched or unbranched, hydrocarbyl chains of 3-12 carbon atoms that further include 1-6 NR or $N(R)_2$ moieties, wherein R is H, ($C_1$-$C_4$) alkyl, phenyl, or benzyl. Polyamines can be linked to an antibody using the cross-linking techniques described above.

Diagnosis or Treatment of a CNS Disorder

Compositions of the invention can be formulated with a pharmaceutically acceptable carrier and administered to a mammal. For example, a composition of the invention can be administered to a non-human animal (e.g., a transgenic mouse model of Alzheimer's disease), or to a human to aid in the diagnosis of a CNS disorder such as Alzheimer's disease or for treating a human patient that has been diagnosed with a CNS disorder. As used herein, the term "treatment" or "treating" refers to administering a composition of the invention to a patient, regardless of whether the patient responds to the treatment, with the proviso that when the same composition is administered to a population of patients, a statistically significant number of patients within the population exhibit a clinically recognized improvement or stabilization of one or more clinical features of the disorder.

In general, compositions of the invention are administered intravenously (i.v.), although other parenteral routes of administration, including subcutaneous, intramuscular, intraarterial, intranasal, intracarotid, and intrahecal also can be used. Formulations of parenteral administration may contain pharmaceutically acceptable carriers such as sterile water or saline, polyalkylene glycols such as polyethylene glycol, vegetable oils, hydrogenated naphthalenes, and the like.

The dosage of the composition to be administered can be determined by the attending physician taking into account various factors known to modify the action of drugs. These include health status, body weight, sex, diet, time and route of administration, other medications, and any other relevant clinical factors. Typically, the dosage is about 1-3000 μg/kg body weight (e.g., from about 10-1000 μg/kg body weight or 50-500 μg/kg body weight). Therapeutically effective dosages may be determined by either in vitro or in vivo methods.

Treatment of a CNS disorder can be assessed by determining if one or more clinical features of the disorder (e.g., cognitive function, memory, behavior, language skills, motor skills, or rigidity of the patient) improve or are stabilized in the patient.

For diagnosis of a CNS disorder, the composition that is administered to the patient contains at least one polypeptide that is labeled as described above. Presence or absence of the labeled polypeptide (e.g., labeled antibody or labeled Aβpolypeptide) is detected in the CNS in vivo (e.g., in the brain of the patient) using, for example, imaging techniques such as positron emission tomography (PET), gamma-scintigraphy, magnetic resonance imaging (MRI), functional magnetic resonance imaging (FMRI), magnetoencephalography (MEG), and single photon emission computerized tomography (SPECT). MRI is particularly useful as the spatial resolution and signal-to-noise ratio provided by MRI (30 microns) is suitable for detecting amyloid deposits, which can reach up to 200 microns in size. The CNS disorder can be diagnosed based on the presence, for example, of labeled amyloid (e.g., labeled amyloid deposits).

The invention will be further described in the following examples, which do not limit the scope of the invention described in the claims.

EXAMPLES

Example 1

Materials and Methods

Aβ Proteins: Human $A\beta_{1-42}$ was synthesized by using f-moc chemistry in a Perkin-Elmer synthesizer in the Mayo Protein Core Facility. The amino acid sequence of human Aβ is provided in SEQ ID NO:1. Purity of the peptide was evaluated by peptide sequencing and laser desorption mass spectrometry.

Monoclonal Antibody Generation: B-cell hybridomas were generated following the procedure of St. Groths and Scheidegger (*J. Immunol. Methods* 35:1 (1980)) in the Mayo Monoclonal Core Facility. Human $A\beta_{1-42}$ that was aggregated and fibrilized by incubating at 37° C. for 24 hours was used as antigen. Positive subclones were isotyped and cryopreserved and further characterized by ELISA and immunohistochemistry labeling of AD transgenic mouse brain sections. A non-specific, monoclonal antibody was obtained from ATCC HB96 L227 (anti-human Ia).

$PS/V_P$ Measurement at the BBB for Radioiodinated Monoclonal IgG (MoIgG): Aliquots of the proteins (MoIgG or Aβ) were labeled with $^{125}I$ or $^{131}I$ using the chloramine T procedure described by Poduslo et al., *Proc. Natl. Acad. Sci. USA* 9:5705-5709 (1994). $PS/V_P$ measurements were performed as described by Poduslo et al., *Neurobiol. Diseases,* 8:555-567 (2001) and Poduslo et al., *Proc. Natl. Acad. Sci. USA* 89:2218-2222 (1992). The procedure for quantifying BBB permeability of proteins was adapted from the rat to the mouse and included catheterizing the femoral artery and vein of the mouse instead of the brachial artery and vein as for the rat. Because of the smaller blood volume in the mouse, serial sampling of 20 μl of blood from the femoral artery was performed and directly TCA precipitated to generate a whole blood washout curve for the intact protein. Briefly, and I.V. bolus injection of phosphate-buffered saline (PBS) containing $^{125}$I—MoIgG (100 µC) was rapidly injected into the femoral vein in pentobarbital-anesthetized mice. Serial blood samples were collected from the femoral artery over the next 30-120 minutes. At 30-60 seconds before the end of the experiment, the second isotope of radiolabeled protein ($^{125}$I—MoIgG) (100 µC) was administered intravenously to serve as a $V_P$ indicator.

After the final blood sample, the animals were sacrificed, the brain and meninges were removed, and the brain was dissected into the cortex, caudate-putamen (neostriatum), hippocampus, thalamus, brain stem, and cerebellum. Tissue was lyophilized, and dry weights were determined with a microbalance and converted to respective wet weights with wet weight/dry weight ratios previously determined. Tissue and plasma samples were assayed for $^{125}$I and $^{131}$I radioactivity in a two-channel gamma counter (Packard COBRAII) with radioactivity corrected for crossover of $^{131}$I activity into the $^{125}$I channel and background. Data are presented as x̄±SEM values with statistical evaluation using ANOVA with significance accepted at the P<0.05 level. The $V_P$ and PS measurements were calculated as described by Poduslo et al., *Neurobiol. Diseases*, 8:555-567 (2001) and Poduslo et al., *Proc. Natl. Acad. Sci. USA* 89:2218-2222 (1992). All procedures were performed using humane and ethical protocols approved by the Mayo Clinic Institutional Animal Care and Use Committee, in accordance with the National Institute of Health's Guide for the Care and Use of Laboratory Animals. All efforts were made to minimize both the suffering and the number of animals used.

Immune Complex Preparation: Human Aβ42 was incubated with its radioiodinated monoclonal antibody (PC2) or the radioiodinated non-specific monoclonal antibody (L227) for 1 hour at 37° C. in PBS at mole ratios of 10:1, 100:1, or 1000:1. Aliquots were then injected into the femoral vein as an I.V. bolus.

Polyamine Modification of Monoclonal IgG: Modification of the monoclonal antibody (PC2) was performed as described by Poduslo and Curran, *Proc. Natl. Acad. Sci. USA* 89:2218-2222 (1992) and Poduslo and Curran, *J. Neurochem.* 66:1599-1609 (1996). Putrescine (PUT) was covalently attached to carboxylic acids using carbodiimide. Ionization of the carboxylic acid groups was controlled by pH, which in turn controlled the extent of modification with the polyamine.

Example 2

Enhanced Permeability of Polyamine Modified Antibody and Immune Complexes at the BBB The BBB permeability of a non-specific monoclonal antibody (anti-human Ia; L227; $IgG_{1K}$), monoclonal antibody against human $Aβ_{1-42}$ (PC2; $IgG_{1K}$), and the immune complex [(human Aβ42)-L227 or (human Aβ42)-PC2] at various mole ratios was determined in the normal adult mouse (B6SJL) as described in Example 1 by quantifying the permeability coefficient×surface area (PS) product for each protein after correction for the residual plasma volume ($V_P$) occupied by the protein in blood vessels in different brain regions following an I.V. bolus injection. In these experiments, the $V_P$ value was determined with a second aliquot of the same protein radioiodinated with a different isotope of iodine ($^{125}$I vs. $^{131}$I) given 30-60 seconds before the end of the experiment. Using the same test substance allows for an accurate determination of the $V_P$ and corrects for non-specific adherence to capillary walls, which would be characteristic of the protein tested. Similarly, a dual isotope approach allows for the determination of the vascular space in each individual animal. The PS product at the BBB for different radioiodinated proteins is corrected, therefore, for the $V_P$ with a second tracer of the same protein.

The PS product for the non-specific monoclonal antibody (L227) ranged from 0.5-1.1×10$^{-6}$ ml/g/sec in six different brain regions (Table 1). The PS values for the monoclonal antibody to human Aβ 1-42 (PC2) ranged from 0.6-1.4×10$^{-6}$ ml/g/sec in the same brain regions and were not significantly different. $V_P$ values ranged from 12.8-28.4 µl/g for L227 and from 11.8-28.0 µl/g for PC2 and were not significantly different (Table 1). The PS values for both monoclonal antibodies were low and less than that observed for albumin. Both IgG and albumin are considered to be transported at the BBB by passive diffusion or fluid phase endocytosis. In contrast, insulin has very high PS values in mice (27.7-43.0×10$^{-6}$ ml/g/sec) and is transported at the BBB by a receptor-mediated transport. Insulin has a PS product at the BBB that is approximately 28.3-49.9 fold greater than that of the monoclonal antibody to human Aβ42 (PC2). In contrast, the $V_P$ values for insulin and the monoclonal antibody to human Aβ42 (PC2) were similar.

TABLE 1

BBB Permeability for the Immune Complex [(hAβ42)-PC2] is Greater than the Monoclonal Antibody Alone (PC2) or a Non-Specific Monoclonal Antibody (L227)

| | (hAβ42)-L227 | | | (hAβ42)-PC2 | | | |
| --- | --- | --- | --- | --- | --- | --- | --- |
| | L227 n = 7 | 100:1 n = 6 | PC2 n = 14 | 10:1 n = 6 | 100:1 n = 6 | 1000:1 n = 7 | RI 100:1 vs. PC2 |
| PS: ml/g/sec × 10$^6$ | | | | | | | |
| Cortex | 0.49 ± 0.03 | 0.95 ± 0.15 | 0.71 ± 0.10 | 1.26 ± 0.25 | 2.87 ± 0.27*** | 2.74 ± 0.31*** | 4.0 |
| Caudate-Putamen | 0.51 ± 0.05 | 0.63 ± 0.15 | 0.64 ± 0.05 | 1.04 ± 0.13* | 2.33 ± 0.15*** | 2.04 ± 0.08*** | 3.6 |
| Hippocampus | 0.59 ± 0.05 | 0.90 ± 0.25 | 0.70 ± 0.06 | 1.15 ± 0.32 | 2.43 ± 0.32*** | 2.82 ± 0.25*** | 4.0 |
| Thalamus | 0.70 ± 0.06 | 1.05 ± 0.24 | 0.81 ± 0.06 | 1.54 ± 0.19* | 3.21 ± 0.17*** | 3.09 ± 0.31*** | 4.0 |
| Brain Stem | 1.10 ± 0.05 | 1.84 ± 0.30 | 1.38 ± 0.15 | 2.70 ± 0.48* | 4.25 ± 0.31*** | 4.20 ± 0.42*** | 3.1 |
| Cerebellum | 0.82 ± 0.05 | 1.30 ± 0.19 | 0.98 ± 0.10 | 2.36 ± 0.59* | 3.58 ± 0.24*** | 3.89 ± 0.54*** | 4.0 |
| $V_P$: µl/g | | | | | | | |
| Cortex | 21.36 ± 1.73 | 26.62 ± 1.52 | 20.07 ± 1.14 | 24.97 ± 0.36 | 24.70 ± 3.00 | 25.60 ± 1.89 | 1.2 |
| Caudate-Putamen | 12.77 ± 1.45 | 16.15 ± 1.61 | 11.78 ± 0.57 | 17.73 ± 1.99* | 17.54 ± 1.70 | 17.60 ± 1.98* | 1.5 |
| Hippocampus | 20.52 ± 2.09 | 25.31 ± 3.05 | 22.51 ± 0.91 | 27.58 ± 1.84 | 26.06 ± 3.28 | 25.94 ± 2.50 | 1.2 |
| Thalamus | 18.47 ± 1.15 | 25.84 ± 2.70 | 17.37 ± 0.98 | 23.17 ± 1.28* | 26.88 ± 3.37** | 23.13 ± 2.34 | 1.6 |

TABLE 1-continued

BBB Permeability for the Immune Complex [(hAβ42)-PC2] is Greater than the Monoclonal
Antibody Alone (PC2) or a Non-Specific Monoclonal Antibody (L227)

| | (hAβ42)-L227 | | | (hAβ42)-PC2 | | | |
|---|---|---|---|---|---|---|---|
| | L227<br>n = 7 | 100:1<br>n = 6 | PC2<br>n = 14 | 10:1<br>n = 6 | 100:1<br>n = 6 | 1000:1<br>n = 7 | RI<br>100:1 vs. PC2 |
| Brain Stem | 25.14 ± 1.63 | 29.10 ± 2.45 | 23.68 ± 1.72 | 30.34 ± 1.47* | 31.11 ± 2.80 | 22.79 ± 1.44 | 1.3 |
| Cerebellum | 28.43 ± 1.99 | 34.86 ± 2.36 | 27.99 ± 1.85 | 37.32 ± 1.96 | 33.84 ± 3.87 | 30.73 ± 2.36 | 1.2 |

$\bar{X}$ ± SEM
L227: ATCC HB96 (Anti-human Ia) $IgG_{1k}$; BALB/c
PC2: MoAb (Anti-human Aβ42) $IgG_{1k}$; BALB/c
RI: Relative increase of immune complex [(hAβ42)-PC2] vs. MoAb (PC2) at mole ratios of 100:1
PS: Permeability coefficient × Surface area product
$V_p$: Residual Plasma Volume
(hAβ42)-L227 ⎫
(hAβ42)-PC2  ⎬ Immune complex at mole ratios of 10:1, 100:1, or 1000:1

Analysis of variance followed by Bonferroni multiple comparisons; only significant differences shown;
*P < 0.05,
**P < 0.01,
***P < 0.001

Permeability of immune complexes of human Aβ42 with its radioiodinated monoclonal antibody at various mole ratios were assessed as described above. At a mole ratio of 10:1 [(hAβ42)-PC2], a significant increase in the PS at the BBB in four of six brain regions was observed compared with the PS values observed for PC2 alone (Table 1). When the mole ratio was increased to 100:1, highly significant PS values (2.3-4.3× $10^{-6}$ ml/g/sec) were obtained in all brain regions (P<0.001). This represents a 3.1 to 4.0-fold increase in the PS values. In contrast, when human Aβ42 was incubated with the non-specific monoclonal antibody (L227) at the same mole ratio of 100:1, the PS values obtained were not significantly different from that in the absence of the antigen (Table 1). When human Aβ42 was incubated with PC2 at a mole ratio of 1000:1, there was a non-significant decrease in the PS values for most of the brain regions indicating that the receptor for human Aβ42 at the BBB was beginning to be saturated (Table 1). In contrast, the $V_p$ values showed a slight trend toward being increased for the different mole ratios of immune complex compared to the monoclonal antibody, and this reached significance in only a few cases. These studies demonstrate that the BBB permeability for the immune complex of (human Aβ42)-PC2 is greater than the monoclonal antibody alone or the non-specific monoclonal antibody. This suggests that the mechanism by which this antibody is crossing the BBB likely involves a receptor for human Aβ at the BBB.

Example 3

Permeability of Polyamine Modified Antibody at the BBB

In the following series of experiments, PS values ranging from 21.5-33.0×$10^{-6}$ ml/g/sec in six different brain regions (Table 2) were observed for a polyamine modified monoclonal antibody to human Aβ(PC2). These PS values for PUT-PC2 were highly significant (P<0.0001) and ranged from 22.8-37.9 fold higher than the antibody (PC2) alone. Polyamine modification of the monoclonal antibody may allow for better delivery across the BBB. This approach is not dependant upon circulating Aβ levels and may allow for a more dramatic reduction in amyloid burden in the Alzheimer brain following passive immunization.

TABLE 2

BBB Permeability of Polyamine-Modified Monoclonal Antibody
(PUT-PC2) is Greater than the Monoclonal Antibody Alone

| | PC2<br>n = 14 | (PC2)<br>PUT-PC2<br>n = 15 | P | RI |
|---|---|---|---|---|
| PS: ml/g/sec × $10^6$ | | | | |
| Cortex | 0.7 ± 0.1 | 25.1 ± 1.5 | **** | 35.9 |
| Caudate-Putamen | 0.6 ± 0.1 | 21.5 ± 1.4 | **** | 35.8 |
| Hippocampus | 0.6 ± 0.1 | 26.5 ± 1.8 | **** | 37.9 |
| Thalamus | 0.8 ± 0.1 | 27.1 ± 1.6 | **** | 33.9 |
| Brain Stem | 1.4 ± 0.2 | 31.9 ± 3.3 | **** | 22.8 |
| Cerebellum | 1.0 ± 0.1 | 33.0 ± 2.3 | **** | 33.0 |
| $V_p$: μl/g | | | | |
| Cortex | 20.1 ± 1.1 | 17.9 ± 0.7 | ns | 0.9 |
| Caudate-Putamen | 11.8 ± 0.6 | 9.8 ± 0.4 | * | 0.8 |
| Hippocampus | 22.5 ± 1.0 | 18.3 ± 1.0 | ns | 0.8 |
| Thalamus | 17.4 ± 1.0 | 17.0 ± 0.8 | ns | 1.0 |
| Brain Stem | 23.7 ± 1.7 | 21.9 ± 1.2 | ns | 0.9 |
| Cerebellum | 28.0 ± 1.9 | 23.7 ± 0.8 | ns | 0.8 |

$\bar{X}$ ± SEM
PC2: MoAb (Anti-human Aβ42) $IgG_{1k}$; BALB/c
PUT-PC2: Putrescine-modified PC2
RI: Relative increase of immune complex [(hAβ42)-PC2] vs. MoAb (PC2) at mole ratios of 100:1
PS: Permeability coefficient × Surface area product
$V_p$: Residual Plasma Volume
$V_p$: Residual Plasma Volume
Analysis by two-tailed unpaired t-test. Ns, not significant (P > 0.05);
* P < 0.05;
**** P < 0.0001

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A therapeutic composition comprising an amyloid-beta (Aβ) polypeptide linked to an anti-Aβ antibody, and a sterile pharmaceutically acceptable carrier or excipient,
    wherein the antibody is polyamine modified and has specific binding affinity for amyloid peptide of SEQ ID NO:1,
    wherein the anti-Aβ antibody improves or stabilizes one or more clinical features of a CNS disorder in a patient,
    wherein the clinical features of a CNS disorder are selected from the group consisting of cognitive function, memory, behavior, language skills, motor skills and patient rigidity.

2. The composition of claim 1, wherein the antibody is a monoclonal polyamine modified antibody.

3. The composition of claim 1, wherein the polyamine modified anti-Aβ antibody is a humanized antibody.

4. The composition of claim 1, wherein the polyamine modified anti-Aβ antibody comprises a Fab fragment.

5. The composition of claim 1, wherein the polyamine modified anti-Aβ antibody comprises a F(ab)₂ fragment.

6. The composition of claim 1, wherein the polyamine modified anti-Aβ antibody comprises a single chain Fv antibody fragment.

7. The composition of claim 1, wherein the polyamine modified anti-Aβ antibody is labeled with a radioisotope or a contrast agent.

8. The composition of claim 1, wherein the polyamine modified anti-Aβ antibody is labeled with a contrast agent.

9. A therapeutic composition comprising an amyloid-beta (Aβ) polypeptide linked to an anti-Aβ antibody, and a sterile pharmaceutically acceptable carrier or excipient,
    wherein the antibody is polyamine modified and has specific binding affinity for amyloid peptide of SEQ ID NO:1,
    wherein the anti-Aβ antibody improves or stabilizes one or more clinical features of a CNS disorder in a patient,
    wherein the clinical features of a CNS disorder are selected from the group consisting of cognitive function and patient rigidity.

* * * * *